United States Patent
Brugger et al.

(10) Patent No.: US 6,649,063 B2
(45) Date of Patent: Nov. 18, 2003

(54) METHOD FOR PERFORMING RENAL REPLACEMENT THERAPY INCLUDING PRODUCING STERILE REPLACEMENT FLUID IN A RENAL REPLACEMENT THERAPY UNIT

(75) Inventors: James M. Brugger, Newburyport, MA (US); Jeffrey H. Burbank, Boxford, MA (US); Dennis M. Treu, Bedford, NH (US)

(73) Assignee: NxStage Medical, Inc., Lawrence, MA (US)

( * ) Notice: Subject to any disclaimer, the term of this patent is extended or adjusted under 35 U.S.C. 154(b) by 87 days.

(21) Appl. No.: 09/905,246

(22) Filed: Jul. 12, 2001

(65) Prior Publication Data

US 2003/0010719 A1 Jan. 16, 2003

(51) Int. Cl.[7] .............................................. B01D 61/00
(52) U.S. Cl. ...................... 210/650; 210/645; 210/646; 210/649; 210/651; 210/739
(58) Field of Search ................................. 210/645, 646, 210/649, 650, 651, 739

(56) References Cited

U.S. PATENT DOCUMENTS

| | | | |
|---|---|---|---|
| 3,697,418 A | | 10/1972 | Johnson |
| 4,468,329 A | | 8/1984 | Shaldon et al. |
| 4,702,829 A | | 10/1987 | Polaschegg et al. |
| 5,114,580 A | | 5/1992 | Ahmad et al. |
| 5,178,763 A | * | 1/1993 | Delaunay ................... 210/644 |
| 5,194,157 A | | 3/1993 | Ghezzi et al. |
| 5,312,547 A | | 5/1994 | Kruger et al. |
| 5,460,446 A | | 10/1995 | Chevallet et al. |
| 5,476,592 A | | 12/1995 | Simard |
| 5,702,597 A | | 12/1997 | Chevallet et al. |
| 5,808,181 A | * | 9/1998 | Wamsiedler et al. ........ 210/646 |
| 6,039,877 A | | 3/2000 | Chevallet et al. |
| 6,042,784 A | * | 3/2000 | Wamsiedler et al. .......... 422/44 |
| 6,132,616 A | | 10/2000 | Twardowski et al. |
| 6,146,536 A | | 11/2000 | Twardowski |
| 6,280,632 B1 | * | 8/2001 | Polaschegg ................. 210/739 |

FOREIGN PATENT DOCUMENTS

| | | |
|---|---|---|
| WO | WO 97/11770 | 4/1997 |
| WO | WO 98/16269 | 4/1998 |
| WO | WO 98/30258 | 7/1998 |
| WO | WO 01/02035 A1 | 1/2000 |

OTHER PUBLICATIONS

"Guidance for the Content of Premarket Notifications for Hemodialysis Delivery Systems," U.S. Department Of Health And Human Services, Food and Drug Administration, Center for Devices and Radiological Health, Aug. 7, 1998, pp. 12–14.

* cited by examiner

*Primary Examiner*—John Kim
(74) *Attorney, Agent, or Firm*—Proskauer Rose LLP

(57) ABSTRACT

A method and device for renal replacement therapy is described that sterile-filters solution that can subsequently be used as a replacement fluid in the same unit. The devices and methods include a pump that can be reversed from its normal forward-pumping direction to sterilize a container of replacement fluid to produce sterile replacement fluid. The sterile replacement fluid is captured in a fluid bag. Upon sterilization of the contents of the container, the pump switches to run in its normal forward-pumping direction. The sterile replacement fluid produced by the previous process is now injected into a patient to perform renal replacement therapy. The waste produced during the renal replacement therapy can be trapped in the container that previously held the non-sterile solution. Systems for sterile filtration and subsequent renal replacement therapy that include pre-connected, sterilized, disposable kits for fluid management and batch collection of sterilized fluid are also described.

25 Claims, 9 Drawing Sheets

METHOD FOR PERFORMING RENAL REPLACEMENT THERAPY INCLUDING PRODUCING STERILE REPLACEMENT FLUID IN A RENAL REPLACEMENT THERAPY UNIT

FIELD OF THE INVENTION

The present invention relates generally to medical devices and methods useful for batch sterile-filtering fluid prior to use as a replacement fluid in renal replacement therapies. More particularly, the devices and methods include using a filter such as a hemofilter first for sterile filtration of a replacement fluid to render the fluid sterile, followed by a renal replacement therapy that uses the sterilized fluid for infusion into a patient.

BACKGROUND OF THE INVENTION

Patients undergoing hemofiltration, hemodialysis, hemodiafiltration, ultrafiltration, or other form of renal replacement therapy need replacement fluid, dialysate, or infusate which is free of biological contaminants. Given the large amount of sterile fluid needed by such therapies and the current method of spiking multiple bags of replacement fluid, dialysate, or infusate, there is a risk of touch contamination resulting in the introduction of biological contaminants into the fluids. Making the appropriate connections, then filtering the fluid greatly reduces this risk to the patient. It would be advantageous if the same equipment used in renal replacement therapy, such as hemofiltration, could be reconfigured for on-line decontamination of prepackaged solutions such as dialysate to produce the large volumes of sterilized replacement fluid required for the therapy.

Presently methods to produce volumes of dialysate from tap water are known, but require complex water purification/standardization equipment, since impurities and cleaning additives such as chlorine vary greatly in tap water from municipality to municipality and within a municipality over time. (See Twardowski U.S. Pat. Nos. 6,146,536 and 6,132,616.)

Moreover, dialysate solution, whether prepared online or prepackaged, while of the proper concentration for use as a sterile replacement fluid, is not deemed to be sufficiently free of pathogenic contaminants to allow the injection of such a fluid into a patient. In hemodialysis, the dialysate never enters the patient's body, but instead flows past a semipermeable membrane that permits impurities in the blood to osmose through the membrane from the higher concentration blood to the lower concentration dialysate. Thus dialysate, intended for extracorporeal use only, is less expensive than solutions prepared as replacement fluids, which will be injected into a patient.

Attempts to render dialysate sufficiently sterile for use as a replacement fluid in hemofiltration and hemodiafiltration have focused on a continuous sterilization process that requires a separate dialysate filtration/purification apparatus that must be periodically purged and verified to provide sufficient constant flow of sterile replacement fluid required for hemofiltration. (See Chavallet U.S. Pat. Nos. 6,039,877 and 5,702,597.) Such devices are necessarily complicated and require separate pumping systems for the sterilization process.

However, if dialysate or other fluid of similar physiological make up could be converted to sterile replacement fluid in the same filter used for hemofiltration or hemodiafiltration, utilizing the same pumps, and without the need for periodic quality-controlled filter purging, a renal replacement therapy unit could be made significantly more simple for reconfiguration to a hemofiltration process to produce low cost sterile replacement fluid in situ. Moreover, the ready availability of pre-connected, disposable filtration and fluid pathway kits that have been sterilized and sealed by the manufacturer would significantly reduce the opportunity for touch contamination during the preparation of sterile replacement fluid.

SUMMARY OF THE INVENTION

The present invention provides devices and methods for producing sterile replacement fluid in a unit that is subsequently used for renal replacement therapy on a patient. The system can be used both to sterilize non-sterile fluid and to sterilize sterile fluid contaminated (e.g., by touch contamination) during connection due to improper technique. In a first embodiment, a system is provided to perform a method that includes the steps of providing a renal replacement therapy unit that has a filter with a membrane separating a waste side of the filter from a clean side. The membrane has a pore size smaller than the non-sterile and pyrogenic material to be filtered. The renal replacement therapy unit also includes a first container of a solution of suitable concentration for use as a replacement fluid that may include the non-sterile and/or pyrogenic material, or sterile fluid contaminated (e.g., by touch contamination) during connection due to improper technique. The first container is in fluid communication with the waste side of the filter. The unit also includes a second container that is adapted to hold sterile replacement fluid. The second container is in fluid communication with the clean side of the filter. A pump, generally the ultrafiltrate pump, is in fluid communication with the first container and the second container. The pump is capable of switching between a first direction that pumps fluid out of the first container and a second direction that removes waste from blood. A second pump, called a replacement fluid pump, pumps fluid out of the second container. The method further includes the step of running the pump in the first (reverse) direction to pump the solution of suitable concentration from the first container into the waste side of the filter. The solution from the first container is filtered through the membrane of the filter to trap the non-sterile and pyrogenic material on the waste side of the filter and produce sterile replacement fluid in the clean side of the filter. The sterile replacement fluid that flows from the clean side of the filter is collected in the second container. During therapy the pump switches to run in the second (forward) direction to pump waste from the blood. The sterile replacement fluid is pumped from the second container into the blood by a second pump. The sterile replacement fluid is used to perform renal replacement therapy on a patient.

Another embodiment is a pre-connected, sterilized fluid management kit for use in presterilizing replacement fluids prior to renal replacement therapy. The kit includes various disposable components of a renal replacement therapy unit. In one embodiment, the kit includes a fluid pumping and balancing system, a sterile fluid reservoir, a plurality of tubes conventionally used in a renal replacement therapy, and a replacement fluid container. Each of the plurality of tubes has a first end in fluid communication with the fluid pumping and balancing system and a second end releasably coupled to and in fluid communication with the sterile fluid reservoir. The replacement fluid container tube has a first end coupled to the fluid pumping and balancing system and a second end adapted to couple to a replacement fluid container. The kit is sterilized and packaged in a container at the time of manufacturing to prevent contamination prior to use in a renal replacement therapy unit.

Another embodiment is a system for batch sterilization of replacement fluid and renal replacement therapy using the sterilized fluid. The system includes a renal replacement therapy unit adapted to releasably receive a sterilized kit and a sterilized kit having preconnected disposable elements of the renal replacement therapy unit. The kit includes a fluid pumping and balancing system, a plurality of connectors, each having a first end coupled to the fluid pumping and balancing system and a second end adapted to releasably couple to the renal replacement therapy unit, a sterile replacement fluid container releasably coupled to the fluid pumping and balancing system through a plurality of tubes, and a tube having a first end coupled to the fluid pumping and balancing system and a second end adapted to releasably couple to a container of solution to be sterilized.

Another embodiment is a method for producing sterile replacement fluid in a renal replacement therapy unit. The method includes the steps of providing a renal replacement therapy unit, a sterilized kit that includes certain disposable elements of the unit, and a container of solution of suitable concentration for use as a replacement fluid. The unit is adapted to releasably receive the sterilized kit. The kit includes a plurality of tubes adapted to releasably couple to the renal replacement therapy unit, a preconnected sterile replacement fluid container and a tube having an end adapted to releasably couple to the solution container. The method further includes the steps of releasably coupling the sterilized kit to the renal replacement therapy unit, releasably coupling the tube to the container of a solution of suitable concentration for use as a replacement fluid, pumping the solution through the renal replacement therapy unit to sterilize it, and capturing the sterilized solution in the sterile replacement fluid container for use in renal replacement therapy.

DETAILED DESCRIPTION

Figure 1:
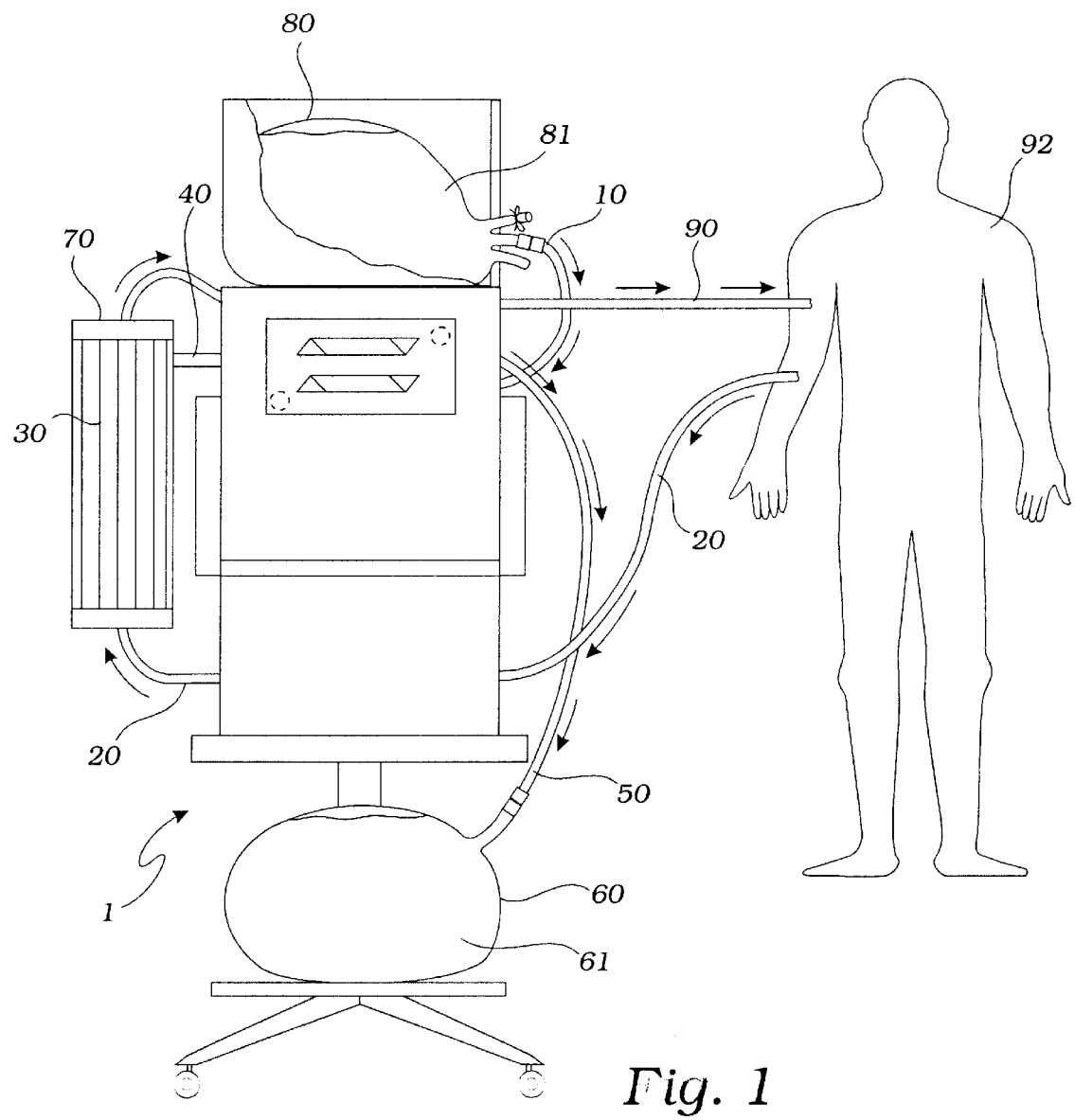
FIG. 1 depicts an embodiment of a hemofiltration unit performing the therapy.

A hemofiltration device 1 is depicted in FIG. 1. In a conventional forward pumping hemofiltration mode, a draw blood line 20 carries blood, for example arterial blood, from the patient 92 to a filter 30. A membrane in the filter 30 allows waste products such as urea and other undesirable metabolic byproducts that are blood contaminants together with water to pass through the filter membrane to the waste side of the filter 30 and out a side port 40 into a waste line 50. The waste line 50 drains the waste filtrate 61 into a waste container 60. The filter membrane does not permit blood cells and higher molecular weight proteins to pass through with the waste filtrate and thus concentrated, purified blood passes out the filter top port 70. The fluid volume lost as waste filtrate during the hemofiltration process must now be replaced in the concentrated, purified blood to return the blood to its proper physiologic concentration. Accordingly, a measured volume of sterile replacement fluid 81 from a sterile fluid reservoir 80 is added to the filtered blood in an amount equal to the volume of waste filtrate removed during the hemofiltration process. A fluid balancing system (not shown in FIG. 1) that measures the waste filtrate removed and then dispenses the proper volume of replacement fluid needed is located inside the hemofiltration unit 1. Systems and devices for fluid balancing have been described in U.S. patent application Ser. No. 09/513,773, filed Feb. 25, 2000, U.S. Pat. No. 6,579,258,the contents of which are incorporated herein in their entirety by reference. The replacement fluid flows from the replacement sterile fluid reservoir 80, through the replacement fluid line 10, to the balancing system in the hemofiltration unit 1. The reconstituted blood, now consisting of the concentrated, purified blood and the measured amount of replacement fluid, is returned via the return blood line 90, for instance a venous line, to the patient 92.

Figure 2A:
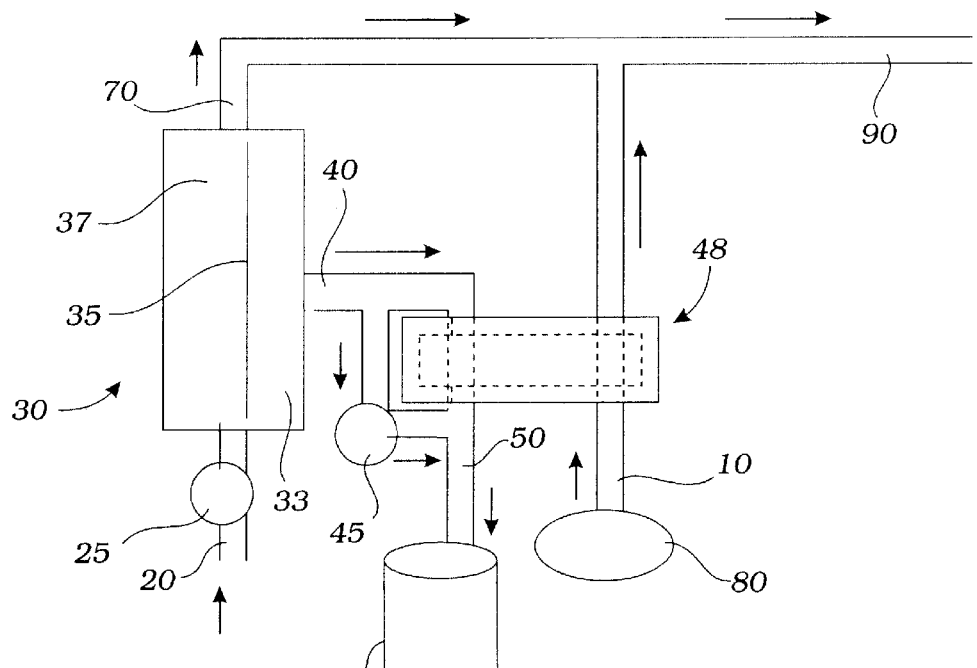
FIG. 2A is a schematic of the embodiment of FIG. 1, performing hemofiltration therapy.

FIG. 2A shows a schematic representation of the hemofiltration process. A draw blood line 20 carries blood from the patient to the filter 30. The blood pump 25 pushes the blood through the filter, and the pressure differential due to the positive pressure of the blood drives the blood across the membrane. A balancing system 48 meters the waste or blood, water, and contaminants through the membrane 35 of the filter 30, metering out the blood, water, and contaminants into the waste side 33 of the filter and allowing concentrated purified blood to pass out the clean side 37 of the filter and into the filter top port. 70. The waste filtrate exits the waste port 40 of the filter 30 and passes into the balancing system 48. Sterile replacement fluid flows from the sterile replacement fluid reservoir 80 through the replacement fluid line 10 to the balancing system 48 where a measured amount of sterile replacement fluid equal to the amount of waste filtrate passed through the balancing system 48 is allowed to combine with the concentrated blood in the return line 90 and return to the patient. The waste filtrate that has passed through the balancing system passes through the waste line 50 and into the waste container 60.

If the therapy requires hemofiltration and ultrafiltration, then an ultrafiltration pump 45 removes excess fluid from the patient's blood and dumps the excess fluid into the waste container 60. This excess fluid removed by the ultrafiltration pump 45 does not pass through the balancing system and thus is not matched by an equal amount of replacement fluid. The system may use additional pumps such as a waste pump and a replacement fluid pump as part of the fluid balancing system to assist the proper fluid flow through the system.

Figure 3:
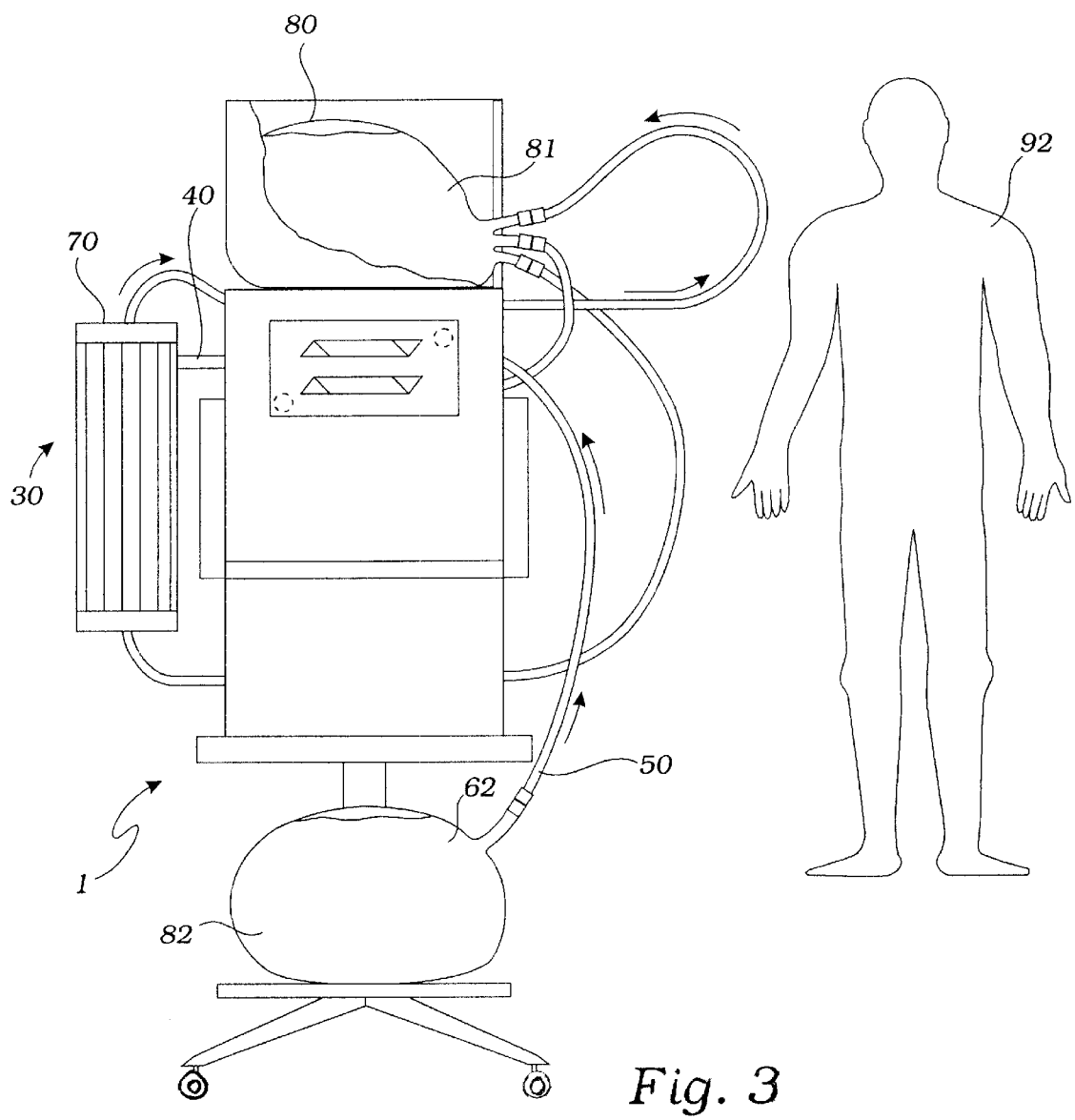
FIG. 3 is an embodiment of a hemofiltration unit operating in the reverse pumping mode used for solution sterilization

FIG. 3 shows an embodiment of the present invention prior to connection to the patient 92 to perform therapy. The hemofiltration unit 1 is configured to convert a solution of suitable electrolyte concentration for use as a replacement fluid 82, for example dialysate, in a container 62 to sterile replacement fluid 81 that is pumped to a container adapted to hold the sterile fluid, such as a sterile fluid reservoir 80, via a filtration sterilization process. While the solution 82 to be converted will have the proper electrolyte concentration required of replacement fluids, there is a concern that the solution will include non-sterile and/or pyrogenic material, for example pathogens such as bacteria, and thus not be sufficiently sterile to be injected into a patient as a replacement fluid. Thus, the hemofiltration unit can be used to filter the solution to remove bacteria and other pathogens and to prepare sterile replacement fluid for a subsequent hemofiltration procedure by running the appropriate pump in the hemofiltration unit in reverse of the pumping mode used for conventional hemofiltration. In a preferred embodiment, the hemofiltration unit is adapted to receive certain disposable components including a fluid pumping and balancing system as more fully explained herein.

Figure 2B:
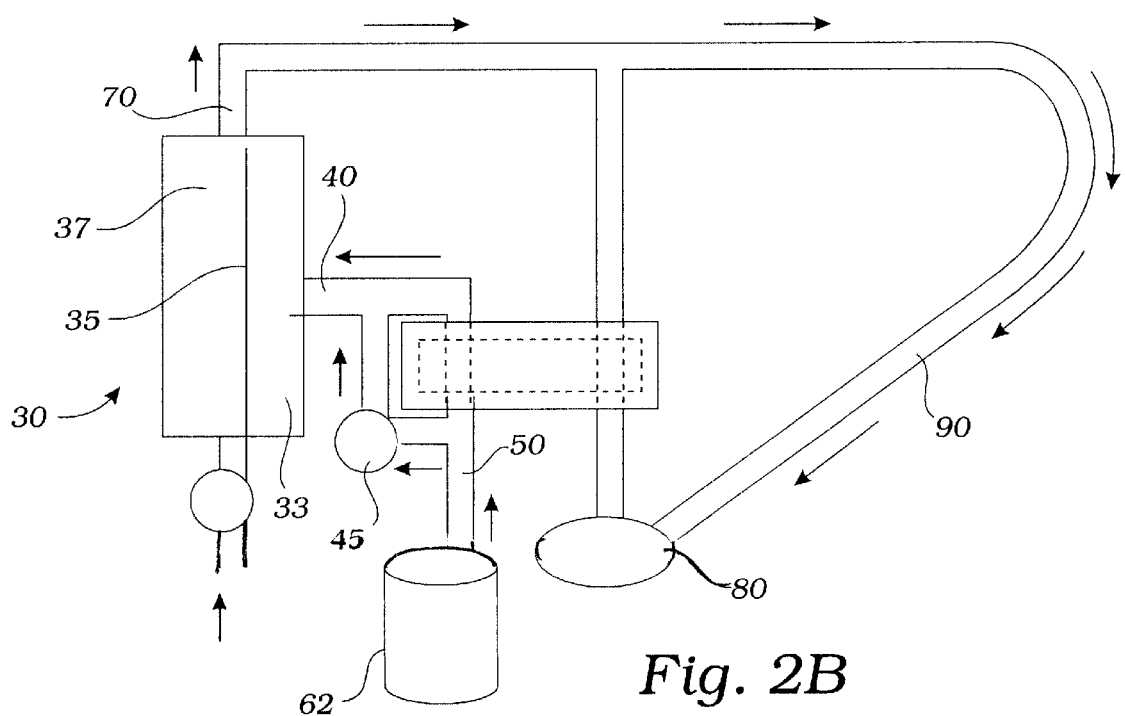
FIG. 2B is a schematic of the embodiment of FIG. 3 performing solution sterilization.

FIG. 2B shows the fluid sterilization process schematically. A pump in fluid communication with the fluid container 62, for instance an ultrafiltration pump 45, is run in reverse of the direction that the pump is conventionally run during ultrafiltration therapy to draw fluid from the container 62 up through the waste line 50 and into the waste side 33 of the filter 30 via the waste port 40. The pump 45 forces the fluid through the filter membrane 35 into the clean side 37 of the filter. Because the non-sterile material in the fluid, for instance bacteria or pyrogen, is larger than the pore size of the filter membrane 35, bacteria in the fluid remain on the waste side 33 of the filter. The filtered fluid, now rendered sterile, emerges as sterile replacement fluid from the top port 70 of the filter and flows through the return blood line 90 into the sterile replacement fluid reservoir 80.

Figure 3A:
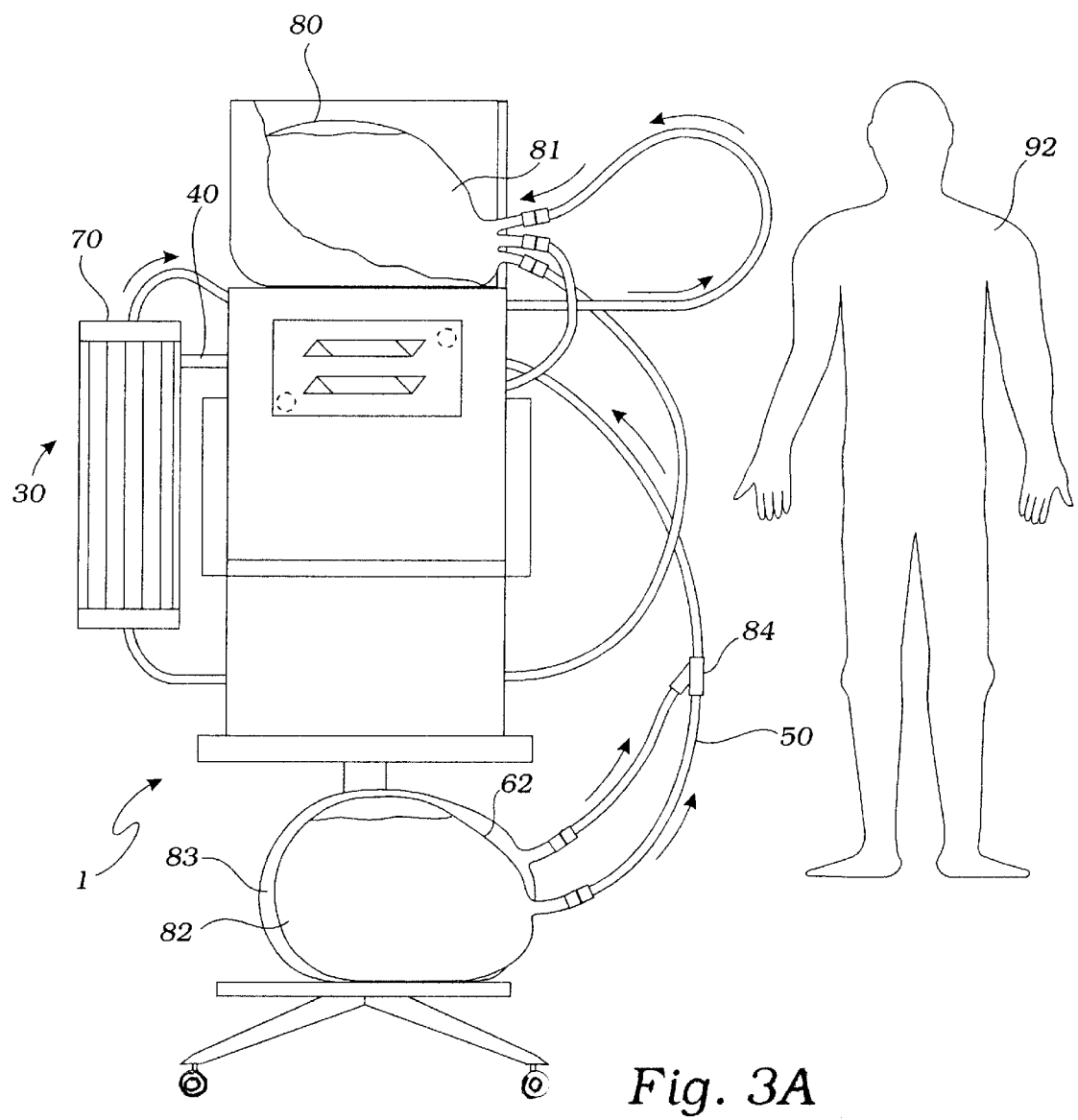
FIG. 3A depicts an embodiment of a hemofiltration unit used to mix dialysate.

In other methods, the user mixes the dialysate and then sterilizes it as shown in FIG. 3A. A first container 82 of concentrated electrolytes, e.g., any one or more of sodium lactate, potassium, calcium, magnesium chloride, sodium chloride, bicarbonate, and/or other appropriate salts, and/or other elements, is connected to Y-connector 84. A second container 83 of water, ringers lactate, or saline is also connected to the Y-connector. The two solutions are then mixed as they pass through Y-connector 84 and then pass through the filter.

The hemofiltration unit automatically primes the remainder of the fluid pathway when all of the replacement fluid is transformed into sterile replacement fluid. The priming process is described more fully herein.

Once the fluid pathway is primed, the hemofiltration unit is ready to be connected to the patient for renal replacement therapy. Referring again to FIGS. 1 and 2A, the blood pump 25 pumps the patient's blood through the filter 30, the balancing system 48 meters fluid from the sterile fluid reservoir 80, and the trapped bacteria on the waste side 33 of the filter pass into the container 60 along with waste blood water. In a preferred embodiment, the now-empty container 60 previously containing the solution 82 can now be used as a waste container for the hemofiltration therapy. A system using more than one filter can also be employed. Further, the system can be used to mix a concentrate solution with another solution.

While the embodiments shown are described for hemofiltration therapy, the devices and methods can be used for blood processing, infusive therapies, or any renal replacement therapy, for instance hemodiafiltration, and can also be used for hemodialysis. Moreover, while the hemofiltration unit described is a volumetric system, this method can be readily employed with a mass-metric hemofiltration system that uses scales instead of balance chambers or flow meters to balance flows.

In a preferred embodiment, the fluid pumping and balancing system and optionally other elements may be preconnected, prepackaged, sterilized and sealed by the manufacturer into a disposable unit such as a kit to reduce touch contamination that can be introduced during set-up of the fluid sterilization process. A renal therapy unit is adapted to receive the kit, which is releasably coupled to the unit, to form a system for batch sterilization of replacement fluid and subsequent renal replacement therapy using the sterilized fluid. Following therapy, the kit may be removed and discarded and a new kit can be installed for a subsequent fluid sterilization and therapy procedure.

Figure 4:
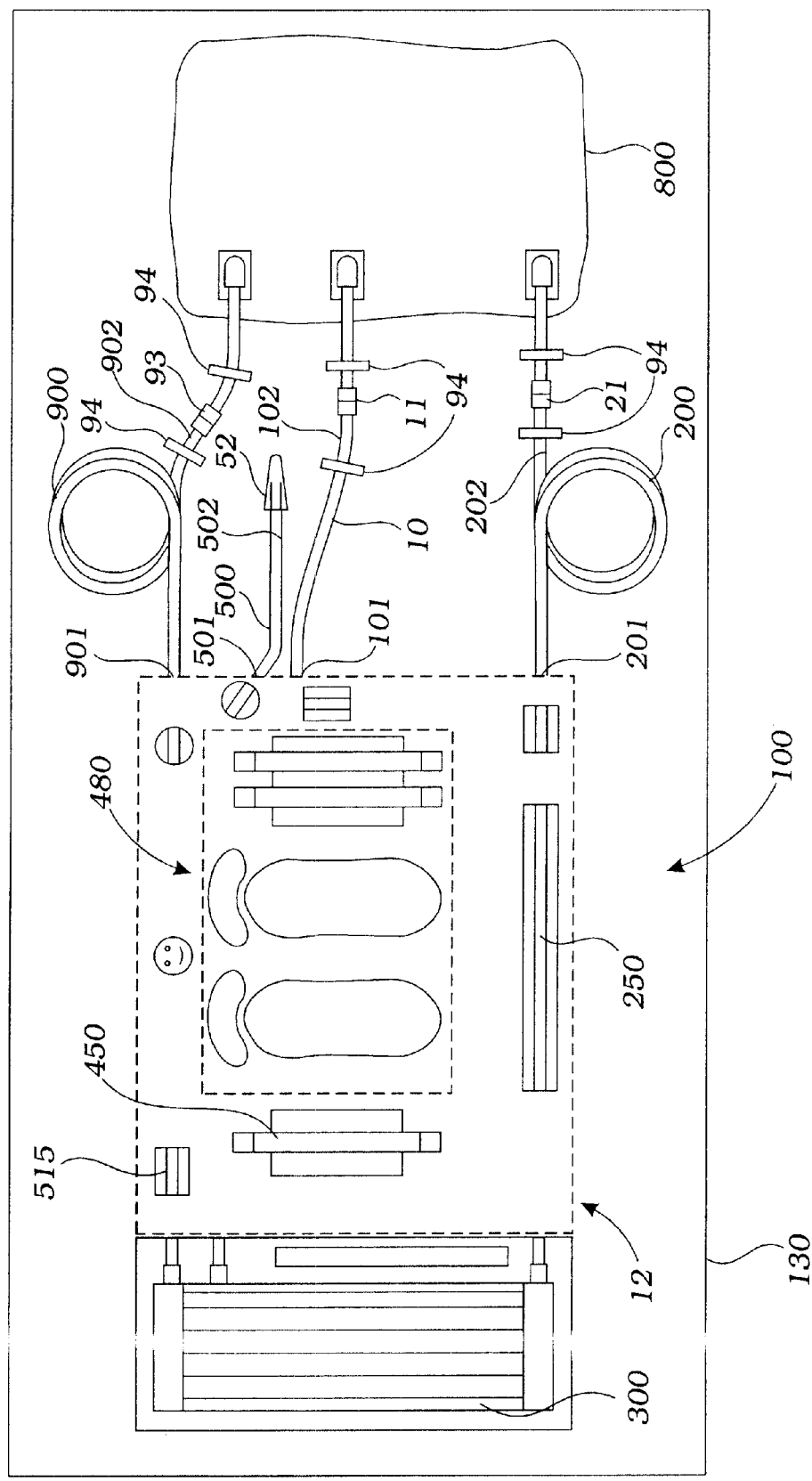
FIG. 4 is another embodiment of a disposable unit adapted to couple to a hemofiltration unit for solution sterilization, priming, and subsequent hemofiltration therapy.

FIG. 4 shows an embodiment of a pre-connected, disposable fluid management kit 100. The embodiment includes a filter 300, for example a hemofilter, and a sterile fluid reservoir 800 connected to a fluid pumping and balancing system 12 through various tubes or lines 900, 10, 200. A first end 901, 101, 201 of each tube 900, 10, 200 is coupled to the fluid pumping and balancing system 12 and a second end 902, 102, 202 of each tube 900, 10, 200 is releasably coupled to the sterile fluid reservoir 800 via connectors 93, 11, 21. Manual clamps 94 may also be used to control fluid flow when disconnecting lines. A waste line 500 has a first end 501 coupled to the fluid pumping and balancing system 12 and a second end 502 removably sealed by a cap 52. In the embodiment of FIG. 4, the fluid management kit includes a filter 300 in fluid communication with the pumping and balancing system 12. The pre-coupled, disposable components of the fluid management kit are sterilized by the manufacturer and sealed in a suitable container 130 to guard against contamination. The container 130 may be a poly bag, Tyvek®, paper or other suitable material. The sterilization process used by the manufacturer may be of any conventional method used for sterilizing medical equipment such as gamma irradiation, chemical sterilant such as ethylene oxide, steam, e-beam or the like. The fluid pumping and balancing system 12 of the embodiment of FIG. 4 includes a blood pump 250, an ultrafiltrate pump 450, a fluid balancing system 480, and a venous air detector 515. The fluid balancing system 480 illustrated in the embodiment is a volumetric system, however it could also be gravimetric flow meters or other means of fluid balancing. The components of the fluid management kit may be connected to form a fluid pathway in any conventional structure used for hemofiltration and ultrafiltration such as the structures shown in the embodiments of FIGS. 1–3. Similarly, the hemofiltration filter 300 may be integrated into the fluid pathway in any conventional structure. In certain embodiment, the hemofiltration filter is not part of the disposable kit.

In the embodiment of FIG. 4, the sterile fluid reservoir 800 is releasably coupled to the fluid pumping and balancing system 12 through a blood return line 900, a sterile replacement fluid line 10 and a draw blood line 200 through connectors 93, 11, and 21. The connectors 93, 11, and 21 can be Luer connectors, proprietary connectors or any other connectors that will provide a hermetic seal that can be decoupled by a user. The sterile fluid reservoir 800 may be of any size required by the therapy, but preferably between 1 and 75 liters and most preferably between 5 and 50 liters, generally approximately 20 liters. The replacement fluid container line 500 can later be used as a waste line during hemofiltration.

Use of the pre-packaged, sterilized fluid management kit greatly reduces the risk of touch contamination. For instance, in the embodiment of FIG. 4, the only connection that must be made by the user during set up is the connection of the replacement fluid container to the waste line 500. Replacement fluid is commonly provided in one-liter bags, thus requiring up to 50 of more connections to sterilize a sufficient amount of fluid depending on the prescribed therapy. In the embodiment of FIG. 4, all of these connections are made on the waste side of the filter, and accordingly any contamination introduced by the connection procedure is filtered out as the solution moves through the system to the sterile fluid reservoir 800 during batch sterilization.

Figure 5:
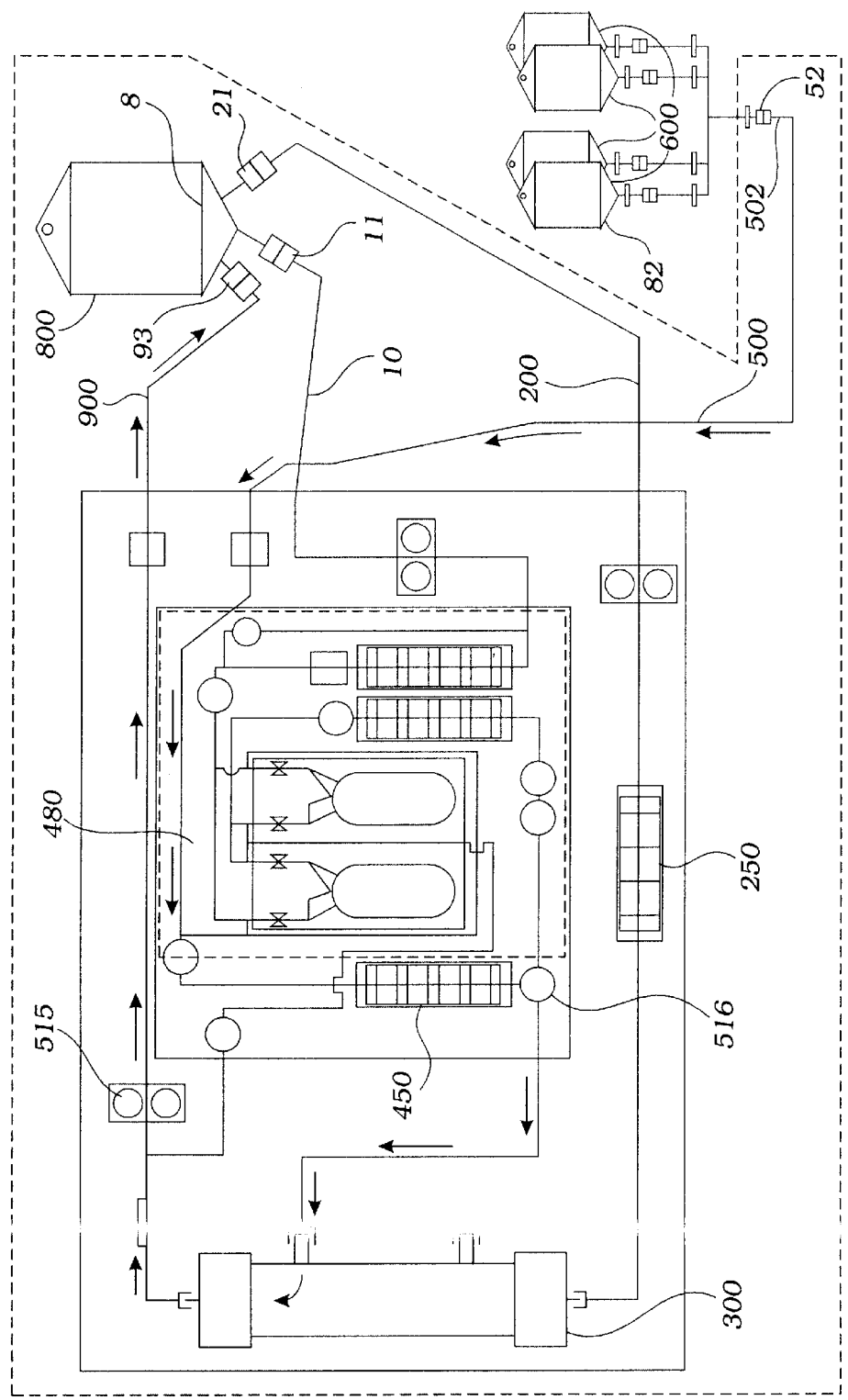
FIG. 5 is an embodiment of a hemofiltration unit performing solution sterilization demonstrating the fluid flow paths.
Figure 7A:
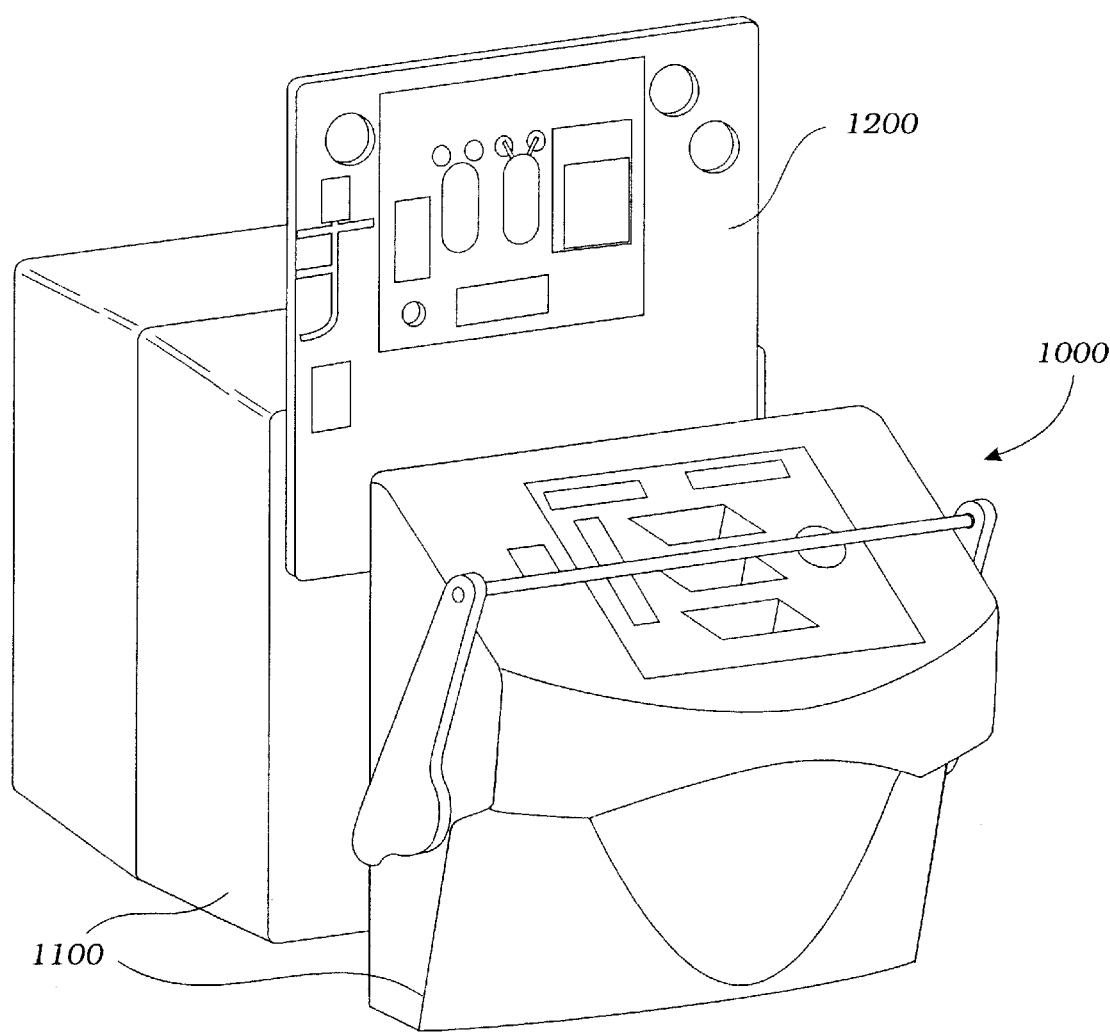
FIG. 7A is an embodiment of a renal replacement therapy system (without tubing) showing the installation of a fluid management kit in a hemofiltration unit adapted to receive the kit.
Figure 7B:
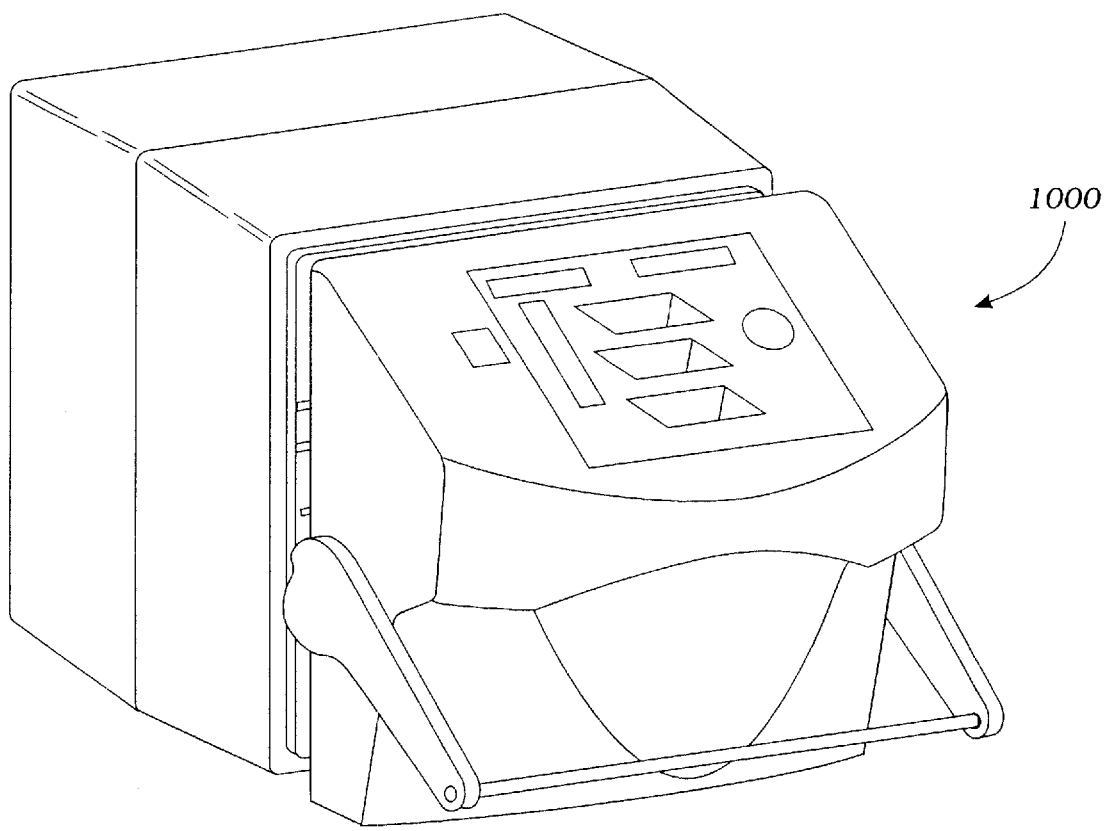
FIG. 7B shows the embodiment of the system of FIG. 7A with the kit fully installed (without tubing).

FIG. 5 shows a schematic of the fluid flow of the fluid management kit 100 of the embodiment of FIG. 4 in use in a system for batch sterilization of replacement fluid and subsequent renal replacement therapy, where the system includes the hemofiltration unit fitted with a disposable fluid management kit. The system is best seen in FIGS. 7A and 7B, where the system 1000 for batch sterilization of replacement fluid and renal replacement therapy using the sterilized fluid includes a renal replacement therapy unit 1100 adapted to releasably receive a sterilized fluid management kit and a sterile fluid management kit 1200 (tubing and bags not shown). FIG. 7A shows the installation of the kit 1200 into the unit 1100. Returning now to FIG. 5, the fluid flow illustrates the batch sterilization process. The second end 502 of the waste line 500 has been releasably coupled to the replacement fluid containers 600. All of the other fluid connectors 93, 11, 21 have been preconnected by the manufacturer and thus are not a source of touch contamination during set-up. Only one pump 450 runs during sterile filtration. All other pumps and the balancing system are dormant during sterile filtration. Sterile filtration continues until the entire batch has been processed.

Figure 6:
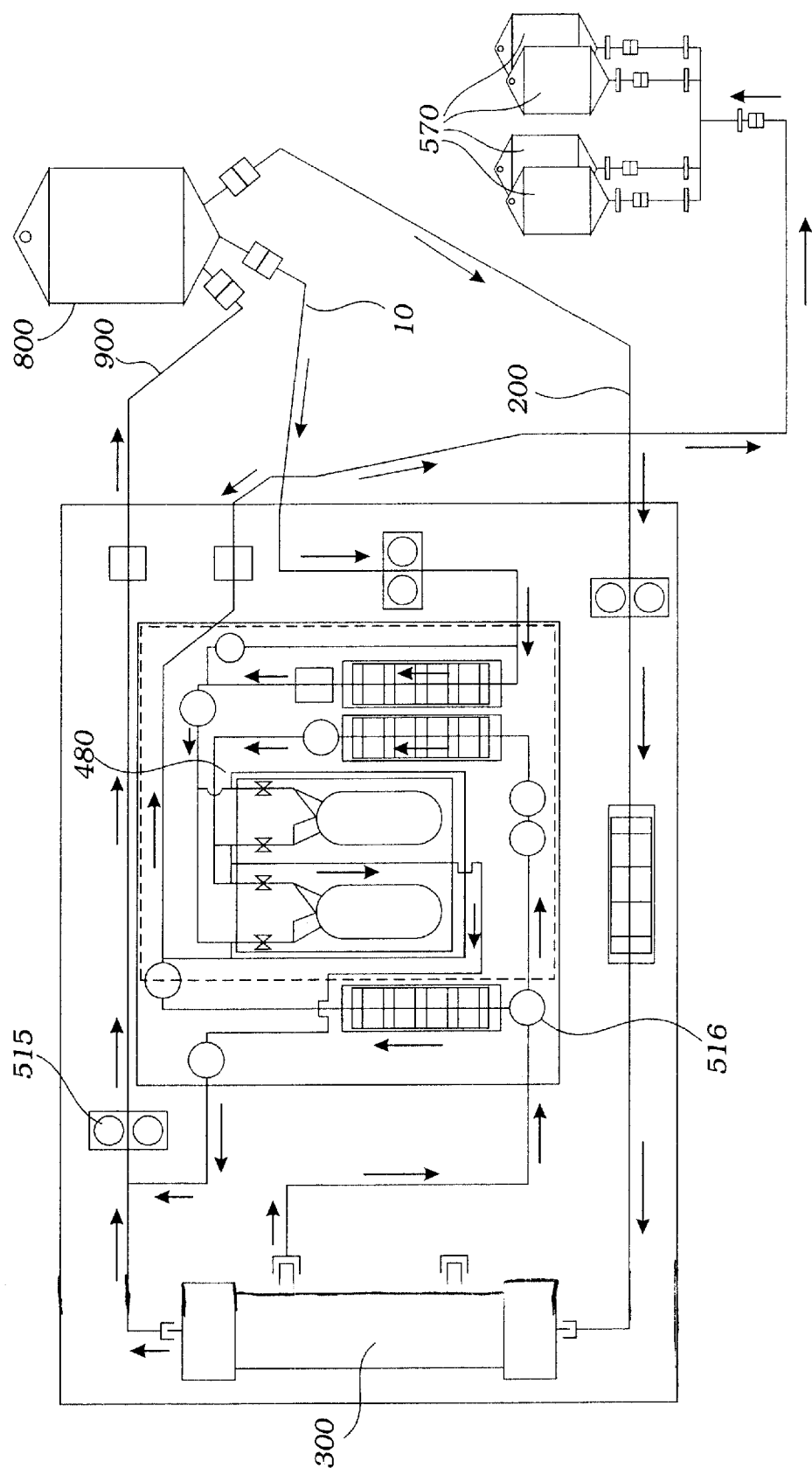
FIG. 6 is an embodiment of a hemofiltration unit in priming mode.

During replacement fluid sterilization, the pump 450, which in this embodiment is the ultrafiltration pump, runs in reverse (a second direction) of its conventional therapeutic pumping direction (a first direction) through filter 300 until the containers 600 of replacement fluid are empty. The emptying of the container results in air pumped into the filter, which is sensed by the venous air detector 515, best seen in FIG. 4. When the venous air detector 515 senses the presence of air, software in the hemofiltration system triggers the pump 450 to reverse the pumping direction to the first direction and to prime the system including the filter. This first direction pumps fluid from the sterile fluid replacement reservoir 800. This priming process is shown in FIG. 6. Since the blood return line 900, the draw line 200 and the replacement fluid line 10 are all connected to the sterile replacement fluid reservoir 800, fluid can be drawn out and air pushed into the reservoir 800 where it floats out of solution. The pump 450 rotates in the forward, or first, pumping direction, metering fluid from the bag 800 and forcing air into the bag 800 from the return line 900. Fluid is drawn through the replacement fluid line 10 and into the fluid balancing system 480 forcing air out into the venous return line 900. Sterile replacement fluid is pushed back across the filter 300 priming the waste side of the filter and dumping air into the former replacement fluid containers, now the waste containers 570. Because the reservoir 800 of sterile replacement fluid acts as a bubble trap, the hemofiltration system, exclusive of the bag, is primed and free of air.

An integrity test can be performed on the filter to verify that the replacement fluid was properly filtered during sterilization. The test, substantially similar to that used in manufacture of the filter itself, measures the partial pressure of the wet filter using the air from the arterial line as the test medium. The replication of the manufacturer's test assures that the filter is leak free and thus the filtered fluid is sterile and safe to use as a replacement fluid.

In certain embodiments, a blood leak detector 516 can be incorporated into the fluid pumping and balancing system and used as a redundant test of filter integrity. If the filter demonstrates a leak after the patient has been connected, the blood leak detector will alarm.

Once a test of filter integrity is successfully performed and the system has been primed as previously described, the unit is ready for renal replacement therapy, for instance hemofiltration or hemodiafiltration. The second end of each of the draw and return lines is decoupled from the sterile replacement fluid reservoir and each is releasably coupled to the appropriate vascular access of the patient and renal replacement therapy is initiated. The vascular access can be a native fistula, a synthetic graft, a catheter a subcutaneous port or other conventionally used method.

Although the foregoing invention has, for the purposes of clarity and understanding, been described in some detail by way of illustration and example, it will be obvious that certain changes and modifications may be practiced that will still fall within the scope of the appended claims. For example, the devices and methods of each embodiment can be combined with or used in any of the other embodiments.

What is claimed is:

1. A method for performing renal replacement therapy including producing sterile replacement fluid in a renal replacement therapy unit, the method comprising the steps of;

providing a renal replacement therapy unit having a filter with a membrane having a pore size smaller than a non-sterile material, the membrane separating a waste side from a clean side of the filter; a first container of a solution, the first container in fluid communication with the waste side of the filter; a second container adapted to hold sterile replacement fluid, the second container in fluid communication with the clean side of the filter; and an ultrafiltration pump in fluid communication with the first container and the second container, the pump capable of switching between a first direction that pumps fluid out of the first container and a second direction that pumps fluid out of the second container;

running the pump in the first direction to pump the solution from the first container into the waste side of the filter;

filtering the solution from the first container through the membrane of the filter to trap the non-sterile material on the waste side of the filter and produce sterile replacement fluid in the clean side of the filter;

collecting the sterile replacement fluid that flows from the clean side of the filter in the second container; and switching the ultrafiltration pump to run in the second direction to pump the sterile replacement fluid from the second container into blood running through the clean side of the filter thereby injecting it into a patient during renal replacement therapy.

2. The method of claim 1, wherein the solution is dialysate solution.

3. The method of claim 1, wherein the solution in the first container is selected from the group consisting of water, ringers lactate, or saline, and wherein the unit further comprises a third container of a concentrated electrolyte solution, the third container in fluid communication with the first container and the waste side of the filter.

4. The method of claim 1, wherein replacement fluid is sterile infusate.

5. The method of claim 1, wherein the renal replacement therapy is hemofiltration.

6. The method of claim 1, wherein the renal replacement therapy is hemodiafiltration.

7. The method of claim 1, wherein the renal replacement therapy is hemodialysis.

8. The method of claim 1, wherein following the step of switching, the method further comprises the step of expelling the non-sterile material and waste into the first container.

9. The method of claim 1, wherein the entire content of the first container is sterilized through the filter membrane before the step of switching the ultrafiltration pump to run in the second direction.

10. The method of claim 9, wherein following the step of switching, the substantially empty first container that previously held the solution of suitable concentration for use as a replacement fluid is now used as a waste container, the method further comprising the step of expelling ultrafiltrate waste material from the waste side of the filter into the waste container during hemofiltration.

11. The method of claim 9, wherein the renal replacement therapy unit further comprises a venous air detector in fluid communication with the first container and the second container, the method further comprising the step of sensing air with the venous air detector upon the sterilization of the entire contents of the first container.

12. The method of claim 11, wherein the step of sensing air occurs prior to the step of switching the direction of the ultrafiltration pump.

13. The method of claim 12, wherein prior to the step of switching the direction of the pump, the method further comprises the step of triggering the switching of the pump when venous air detector senses air.

14. A method for performing renal replacement therapy including producing safe replacement fluid in a renal replacement therapy unit, the method comprising the steps of:

providing a renal replacement therapy unit having a filter with a membrane having a pore size smaller than pyrogenic material, the membrane separating a first side of the filter from a second side;

a source of replacement fluid in fluid communication with the second side of the filter;

a replacement fluid container adapted to hold pyrogen-free replacement fluid, the replacement fluid container in fluid communication wit the first side of the filter; and a pump in fluid communication wit the source of replacement fluid and the replacement fluid container, the pump being capable of switching between a first direction that pumps fluid from the source of replacement fluid and a second direction that pumps fluid out of the replacement fluid container;

running the pump in the first direction to pump the solution from the source of replacement fluid into the second side of the filter;

filtering the solution from the source of replacement fluid through the membrane of the filter to trap pyrogenic material on the second side of the filter and produce pyrogen-free replacement fluid in the first side of the filter;

collecting the pyrogen-free replacement fluid that flows from the first side of the filter in the replacement fluid container; and switching the pump to nut in the second direction to pump the pyrogen-free replacement fluid from the replacement fluid container into a blood line to be injected into a patient during renal replacement therapy.

15. The method of claim 14, wherein the solution is dialysate solution.

16. The method of claim 14, wherein replacement fluid is sterile infusate.

17. The method of claim 14, wherein the renal replacement therapy is hemofiltration.

18. The method of claim 14, wherein the renal replacement therapy is hemodiafiltration.

19. The method of claim 14, wherein the renal replacement therapy is hemodialysis.

20. The method of claim 14, wherein following the step of switching, the method further comprises the step of expelling waste from the second side of the filter.

21. The method of claim 14, wherein the source of replacement fluid includes a source fluid container and the entire contents of the source fluid container is filtered through the filter membrane before the step of switching the pump to run in the second direction.

22. The method of claim 21, wherein, following the step of switching, the substantially empty source fluid container is now used to receive waste, the method further comprising the step of expelling waste from the second side of the filter into the source fluid container during hemofiltration.

23. The method of claim 22, wherein the renal replacement therapy unit further comprises a venous air detector in fluid communication with the replacement fluid container and the source fluid container, the method further comprising the step of sensing air with the venous air detector upon the filtering of the entire contents of the source fluid container.

24. The method of claim 23, wherein the step of sensing air occurs prior to the step of switching the direction of the pump.

25. The method of claim 24, wherein prior to the step of switching the direction of the pump, the method further comprises the step of triggering the switching of the pump when the venous air detector senses air.

* * * * *